United States Patent
Park et al.

(10) Patent No.: US 12,134,646 B2
(45) Date of Patent: Nov. 5, 2024

(54) ANTI-C-KIT ANTIBODY

(71) Applicant: NOVELTY NOBILITY INC., Suwon-si (KR)

(72) Inventors: Sang Gyu Park, Yongin-si (KR); Jin-Ock Kim, Jeungpyeong-gun (KR)

(73) Assignee: NOVELTY NOBILITY INC., Suwon-si (KR)

( * ) Notice: Subject to any disclaimer, the term of this patent is extended or adjusted under 35 U.S.C. 154(b) by 870 days.

(21) Appl. No.: 17/284,672

(22) PCT Filed: Oct. 10, 2019

(86) PCT No.: PCT/KR2019/013310
§ 371 (c)(1),
(2) Date: Apr. 12, 2021

(87) PCT Pub. No.: WO2020/076105
PCT Pub. Date: Apr. 16, 2020

(65) Prior Publication Data
US 2021/0355212 A1 Nov. 18, 2021

(30) Foreign Application Priority Data
Oct. 10, 2018 (KR) .................. 10-2018-0120233

(51) Int. Cl.
*C07K 16/28* (2006.01)
*A61K 39/00* (2006.01)
*A61P 9/00* (2006.01)

(52) U.S. Cl.
CPC ............ *C07K 16/2803* (2013.01); *A61P 9/00* (2018.01); *A61K 2039/505* (2013.01); *C07K 2317/565* (2013.01); *C07K 2317/76* (2013.01)

(58) Field of Classification Search
CPC .......... C07K 16/2803; C07K 2317/565; C07K 2317/76; C07K 2317/24; C07K 2317/33; C07K 2317/92; A61P 9/00; A61P 27/02; A61P 35/00; A61K 2039/505; G01N 2333/71; G01N 33/5748; G01N 33/6893
See application file for complete search history.

(56) References Cited

U.S. PATENT DOCUMENTS

| | | | |
|---|---|---|---|
| 2013/0011406 A1* | 1/2013 | Hadari ................ | A61P 35/00 424/139.1 |
| 2015/0191729 A1 | 7/2015 | Suh et al. | |
| 2018/0193475 A1 | 7/2018 | Abrams et al. | |

FOREIGN PATENT DOCUMENTS

| | | |
|---|---|---|
| JP | 2016-512832 A | 5/2016 |
| KR | 10-2014-0027239 A | 3/2014 |
| KR | 10-1384360 B1 | 4/2014 |
| KR | 10-2015-0038278 A | 4/2015 |
| KR | 10-2015-0131173 A | 11/2015 |
| WO | 2010/136508 A2 | 12/2010 |
| WO | 2012/154480 A1 | 11/2012 |

OTHER PUBLICATIONS

Lerner et al. Monoclonal Antibody YB5.B8 Identifies the HUman c-kit Portein Product. 1991. Blood. 77(9): 1876-7883. (Year: 1991).*
Loukovaara et al. Indications of lymphatic endothelial differentiation and endothelial progenitor cell activation in the pathology of proliferative diabetic retinopathy. 2015. Acta Ophthalmol. 93: 512-523. (Year: 2015).*
Bisht et al. Angiogenesis: Future of pharmacological modulation. 2010. Indian Journal of Pharmacology 42(1):2-8. (Year: 2010).*
Lennartsson et al. Stem cell factor receptor/ c-kit: from basic science to clinical implications. 2012. Physiol Rev 92: 1619-1649. (Year: 2012).*
Felmeden et al. Angiogenesis: basic pathophysiology and implications for disease. 2003. European Heart Journal 24: 586-603. (Year: 2003).*
Yoshida et al., "Therapeutic Efficacy of C-Kit-Targeted Radioimmunotherapy Using 90Y-Labeled Anti-C-Kit Antibodies in a Mouse Model of Small Cell Lung Cancer", PLOS ONE, Mar. 2013, vol. 8, Issue 3, e59248 (8 pages total).
Okayama et al., "Assessment of the anti-c-kit monoclonal antibody YB5.B8 in affinity magnetic enrichment of human lung mast cells", Journal of Immunological Methods, vol. 169, 1994, pp. 153-161(9 pages total).
Lebron et al., "A human monoclonal antibody targeting the stem cell factor receptor (c-Kit) blocks tumor cell signaling and inhibits tumor growth", Cancer Biology & Therapy, vol. 15, Issue 9, 2014, pp. 1208-1218 (11 pages total).
Extended European Search Report dated Jul. 4, 2022 from the European Patent Office in EP Application No. 19870797.8.
So Ra Kim, et al., "The cKit Inhibitor, Masitinib, Prevents Diabetes-Induced Retinal Vascular Leakage", IOVS, Mar. 2016, vol. 57, No. 3, 1201-1206 (6 pages).
Yoshimichi Okayama et al., "Assessment of the anti-c-kit monoclonal antibody YB5.B8 in affinity magnetic enrichment of human lung mast cells", Journal of Immunological Methods, 1994, pp. 153-161, vol. 169, No. 2.
Written Opinion for PCT/KR2019/013310, dated Jan. 22, 2020.
International Search Report for PCT/KR2019/013310, dated Jan. 22, 2020.

* cited by examiner

*Primary Examiner* — Brad Duffy
*Assistant Examiner* — Amber K Faust
(74) *Attorney, Agent, or Firm* — Sughrue Mion, PLLC

(57) ABSTRACT

The present invention relates to a novel anti-C-KIT antibody or an antibody fragment thereof. In addition, the present invention relates to a composition for preventing or treating angiogenesis-related diseases comprising the anti-C-KIT antibody or an antibody fragment thereof, or a kit for diagnosing angiogenesis-related diseases.

11 Claims, 13 Drawing Sheets

Specification includes a Sequence Listing.

FIG. 6

GAT ATT GTG ATG ACT CAG
D   I   V   M   T   Q

TCT CCA CTC TCC CTG CCC GTC ACC CCT GGA GAG CCG GCC TCC ATC
S   P   L   S   L   P   V   T   P   G   E   P   A   S   I

TCC TGC AGG TCT AGT CAG AGC CTC CTG CAT AGT AAT GGA TAC AAC
S   C   R   S   S   Q   S   L   L   H   S   N   G   Y   N
                                CDR1

TAT TTG GAT TGG TAC CTG CAG AAG CCA GGG CAG TCT CCA CAG CTC
Y   L   D   W   Y   L   Q   K   P   G   Q   S   P   Q   L
        CDR2

CTG ATC TAT TTG GGT TCT AAT CGG GCC TCC GGG GTC CCT GAC AGG
L   I   Y   L   G   S   N   R   A   S   G   V   P   D   R

TTC AGT GGC AGT GGA TCA GGC ACA GAT TTT ACA CTG AAA ATC AGC
F   S   G   S   G   S   G   T   D   F   T   L   K   I   S

AGA GTG GAG GCT GAG GAT GTT GGG GTT TAT TAC TGC ATG CAA GCT
R   V   E   A   E   D   V   G   V   Y   Y   C   M   Q   A
                                                    CDR3

CTA CAA ACT ATT ACC TTC GGC CAA GGG ACA CGA CTG GAG ATT AAA
L   Q   T   I   T   F   G   Q   G   T   R   L   E   I   K

FIG. 7

```
CAG GTG CAG CTG GTG GAG TCT GGG GGA GGC GTG
 Q   V   Q   L   V   E   S   G   G   G   V

GTC CAG CCT GGG AGG TCC CTG AGA CTC TCC TGT GCA GCG TCT GGA
 V   Q   P   G   R   S   L   R   L   S   C   A   A   S   G
              CDR1
TTC ACC TTC AGT AGC TAT GGC ATG CAC TGG GTC CGC CAG GCT CCA
 F   T   F   S   S   Y   G   M   H   W   V   R   Q   A   P
                                                  CDR2
GGC AAG GGG CTG GAG TGG GTG GCA GTT ATA TGG TAT GAT GGA ACT
 G   K   G   L   E   W   V   A   V   I   W   Y   D   G   T

AAT AAA GAC TAT ACA GAC TCC GTG AAG GGC CGA TTC ACC ATC TCC
 N   K   D   Y   T   D   S   V   K   G   R   F   T   I   S

AGA GAC AAT TCC AAG AAC ACG CTG TAT CTT CAA ATG AAC AGC CTG
 R   D   N   S   K   N   T   L   Y   L   Q   M   N   S   L
                                                      CDR3
AGA GCC GAG GAC ACG GCT GTG TAT TAC TGT GCG AGA GAA GAT TGG
 R   A   E   D   T   A   V   Y   Y   C   A   R   E   D   W

GCT GAG GCT TTT GAT ATG TGG GGC CAA GGG ACA ACG GTC ACC GTC
 A   E   A   F   D   M   W   G   Q   G   T   T   V   T   V

TCT TCA
 S   S
```

FIG.9
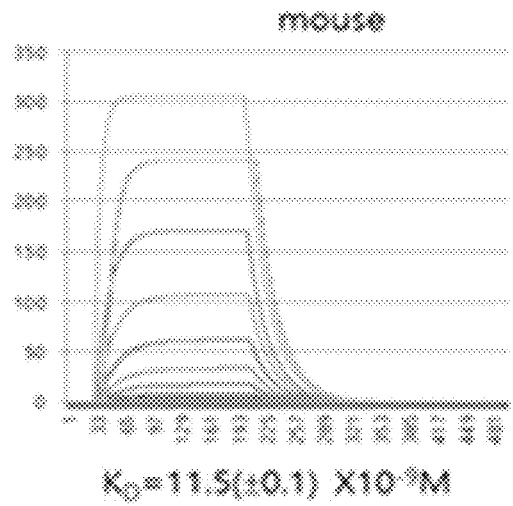
$K_D = 11.5(\pm 0.1) \times 10^{-9} M$
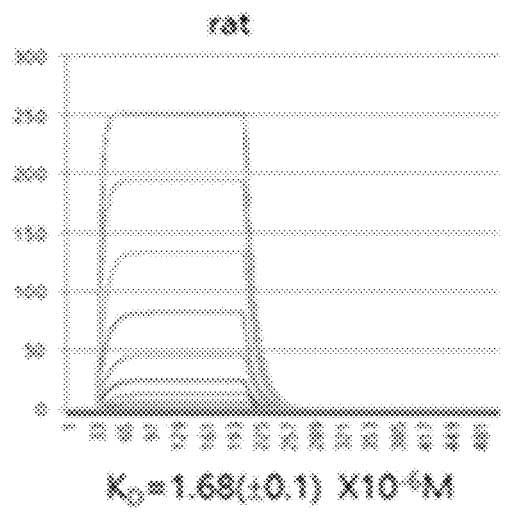
$K_D = 1.68(\pm 0.1) \times 10^{-6} M$
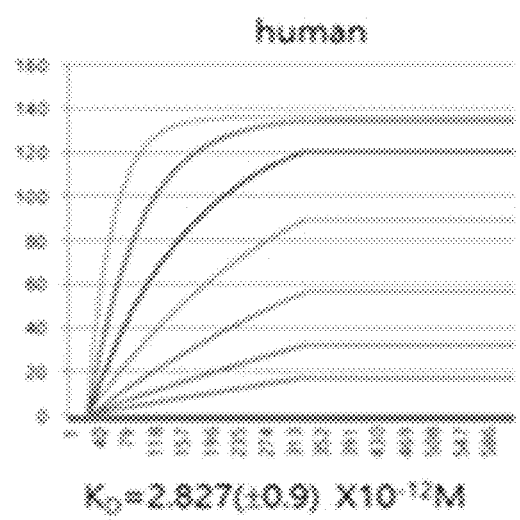
$K_D = 2.827(\pm 0.9) \times 10^{-12} M$

SEQUENCE LISTING

```
<160> NUMBER OF SEQ ID NOS: 30

<210> SEQ ID NO 1
<211> LENGTH: 11
<212> TYPE: PRT
<213> ORGANISM: Artificial Sequence
<220> FEATURE:
```

```
<223> OTHER INFORMATION: CDR1 of 2G4 light chain

<400> SEQUENCE: 1

Gln Ser Leu Leu His Ser Asn Gly Tyr Asn Tyr
1               5                   10

<210> SEQ ID NO 2
<211> LENGTH: 3
<212> TYPE: PRT
<213> ORGANISM: Artificial Sequence
<220> FEATURE:
<223> OTHER INFORMATION: CDR2 of 2G4 light chain

<400> SEQUENCE: 2

Leu Gly Ser
1

<210> SEQ ID NO 3
<211> LENGTH: 8
<212> TYPE: PRT
<213> ORGANISM: Artificial Sequence
<220> FEATURE:
<223> OTHER INFORMATION: CDR3 of 2G4 light chain

<400> SEQUENCE: 3

Met Gln Ala Leu Gln Thr Ile Thr
1               5

<210> SEQ ID NO 4
<211> LENGTH: 8
<212> TYPE: PRT
<213> ORGANISM: Artificial Sequence
<220> FEATURE:
<223> OTHER INFORMATION: CDR1 of 2G4 heavy chain

<400> SEQUENCE: 4

Gly Phe Thr Phe Ser Arg Tyr Gly
1               5

<210> SEQ ID NO 5
<211> LENGTH: 8
<212> TYPE: PRT
<213> ORGANISM: Artificial Sequence
<220> FEATURE:
<223> OTHER INFORMATION: CDR2 of 2G4 heavy chain

<400> SEQUENCE: 5

Ile Trp Tyr Asp Gly Thr Asn Lys
1               5

<210> SEQ ID NO 6
<211> LENGTH: 11
<212> TYPE: PRT
<213> ORGANISM: Artificial Sequence
<220> FEATURE:
<223> OTHER INFORMATION: CDR3 of 2G4 heavy chain

<400> SEQUENCE: 6

Ala Arg Glu Asp Trp Ala Glu Ala Phe Asp Met
1               5                   10

<210> SEQ ID NO 7
<211> LENGTH: 111
<212> TYPE: PRT
<213> ORGANISM: Artificial Sequence
<220> FEATURE:
<223> OTHER INFORMATION: variable domain of 2G4 light chain
```

<400> SEQUENCE: 7

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Ile Thr Phe Gly Gln Gly Thr Arg Leu Glu Ile Lys
            100                 105                 110

<210> SEQ ID NO 8
<211> LENGTH: 118
<212> TYPE: PRT
<213> ORGANISM: Artificial Sequence
<220> FEATURE:
<223> OTHER INFORMATION: variable domain of 2G4 heavy chain

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Thr Asn Lys Asp Tyr Thr Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Ala Glu Ala Phe Asp Met Trp Gly Gln Gly Thr
            100                 105                 110

Thr Val Thr Val Ser Ser
        115

<210> SEQ ID NO 9
<211> LENGTH: 33
<212> TYPE: DNA
<213> ORGANISM: Artificial Sequence
<220> FEATURE:
<223> OTHER INFORMATION: CDR1 of 2G4 light chain

<400> SEQUENCE: 9
cagagcctcc tgcatagtaa tggatacaac tat                              33

<210> SEQ ID NO 10
<211> LENGTH: 9
<212> TYPE: DNA
<213> ORGANISM: Artificial Sequence
<220> FEATURE:
<223> OTHER INFORMATION: CDR2 of 2G4 light chain

<400> SEQUENCE: 10

-continued

```
ttgggttct                                                              9
```

<210> SEQ ID NO 11
<211> LENGTH: 24
<212> TYPE: DNA
<213> ORGANISM: Artificial Sequence
<220> FEATURE:
<223> OTHER INFORMATION: CDR3 of 2G4 light chain

<400> SEQUENCE: 11

```
atgcaagctc tacaaactat cacc                                            24
```

<210> SEQ ID NO 12
<211> LENGTH: 24
<212> TYPE: DNA
<213> ORGANISM: Artificial Sequence
<220> FEATURE:
<223> OTHER INFORMATION: CDR1 of 2G4 heavy chain

<400> SEQUENCE: 12

```
ggattcacct tcagtcgcta tggc                                            24
```

<210> SEQ ID NO 13
<211> LENGTH: 24
<212> TYPE: DNA
<213> ORGANISM: Artificial Sequence
<220> FEATURE:
<223> OTHER INFORMATION: CDR2 of 2G4 heavy chain

<400> SEQUENCE: 13

```
atatggtatg atggaactaa taaa                                            24
```

<210> SEQ ID NO 14
<211> LENGTH: 33
<212> TYPE: DNA
<213> ORGANISM: Artificial Sequence
<220> FEATURE:
<223> OTHER INFORMATION: CDR3 of 2G4 heavy chain

<400> SEQUENCE: 14

```
gcgagagaag attgggctga ggcttttgat atg                                  33
```

<210> SEQ ID NO 15
<211> LENGTH: 333
<212> TYPE: DNA
<213> ORGANISM: Artificial Sequence
<220> FEATURE:
<223> OTHER INFORMATION: variable domain of 2G4 light chain

<400> SEQUENCE: 15

```
gatattgtga tgactcagtc tccactctcc ctgcccgtca cccctggaga gccggcctcc     60
atctcctgca ggtctagtca gagcctcctg catagtaatg gatacaacta tttggattgg   120
tacctgcaga agccaggca gtctccacag ctcctgatct atttgggttc taatcgggcc    180
tccggggtcc ctgacaggtt cagtggcagt ggatcaggca cagattttac actgaaaatc   240
agcagagtgg aggctgagga tgttgggggtt tattactgca tgcaagctct acaaactatc   300
accttcggcc aagggacacg actggagatt aaa                                 333
```

<210> SEQ ID NO 16
<211> LENGTH: 354
<212> TYPE: DNA
<213> ORGANISM: Artificial Sequence
<220> FEATURE:

<223> OTHER INFORMATION: variable domain of 2G4 heavy chain

<400> SEQUENCE: 16
caggtgcagc tggtggagtc tgggggaggc gtggtccagc ctggaggtc cctgagactc    60 tcctgtgcag cgtctggatt caccttcagt cgctatggca tgcactgggt ccgccaggct   120
ccaggcaagg ggctggagtg ggtggcagtt atatggtatg atggaactaa taaagactat   180
acagactccg tgaggggccg attcaccatc tccagagaca attccaagaa cacgctgtat   240
cttcaaatga acagcctgag agccgaggac acggctgtgt attactgtgc gagagaagat   300
tgggctgagg cttttgatat gtggggccaa gggacaacgg tcaccgtctc ttca         354

<210> SEQ ID NO 17
<211> LENGTH: 33
<212> TYPE: DNA
<213> ORGANISM: Artificial Sequence
<220> FEATURE:
<223> OTHER INFORMATION: CDR1 of 2G4 light chain_optimized codon for CHO

<400> SEQUENCE: 17
cagtccctgc tgcactccaa cggctacaac tac                                 33

<210> SEQ ID NO 18
<211> LENGTH: 9
<212> TYPE: DNA
<213> ORGANISM: Artificial Sequence
<220> FEATURE:
<223> OTHER INFORMATION: CDR2 of 2G4 light chain_optimized codon for CHO

<400> SEQUENCE: 18 ctgggctcc                                                             9

<210> SEQ ID NO 19
<211> LENGTH: 24
<212> TYPE: DNA
<213> ORGANISM: Artificial Sequence
<220> FEATURE:
<223> OTHER INFORMATION: CDR3 of 2G4 light chain_optimized codon for CHO

<400> SEQUENCE: 19
atgcaggccc tgcagaccat cacc                                           24

<210> SEQ ID NO 20
<211> LENGTH: 24
<212> TYPE: DNA
<213> ORGANISM: Artificial Sequence
<220> FEATURE:
<223> OTHER INFORMATION: CDR1 of 2G4 heavy chain_optimized codon for CHO

<400> SEQUENCE: 20
ggcttcacct tctccagata cgga                                           24

<210> SEQ ID NO 21
<211> LENGTH: 24
<212> TYPE: DNA
<213> ORGANISM: Artificial Sequence
<220> FEATURE:
<223> OTHER INFORMATION: CDR2 of 2G4 heavy chain_optimized codon for CHO

<400> SEQUENCE: 21
atttggtacg acggcaccaa caag                                           24

<210> SEQ ID NO 22
<211> LENGTH: 33

```
<212> TYPE: DNA
<213> ORGANISM: Artificial Sequence
<220> FEATURE:
<223> OTHER INFORMATION: CDR3 of 2G4 heavy chain_optimized codon for CHO

<400> SEQUENCE: 22
gccagagagg attgggccga agccttcgat atg                              33

<210> SEQ ID NO 23
<211> LENGTH: 333
<212> TYPE: DNA
<213> ORGANISM: Artificial Sequence
<220> FEATURE:
<223> OTHER INFORMATION: variable domain of 2G4 light chain_optimized
      codon for CHO

<400> SEQUENCE: 23
gacatcgtga tgacccagtc tccactgagc ctgcctgtga cacctggcga gcctgcttcc    60
atctcctgca gatcctctca gtccctgctg cactccaacg gctacaacta cctggactgg   120
tatctgcaga agcccggcca gtctcctcag ctgctgatct acctgggctc aaacagagct   180
tctggcgtgc ccgatagatt ctccggctct ggctctggca ccgacttcac cctgaagatc   240
tccagagtgg aagccgagga cgtgggcgtg tactactgta tgcaggccct gcagaccatc   300
accttcggcc agggaaccag actggaaatc aag                               333

<210> SEQ ID NO 24
<211> LENGTH: 354
<212> TYPE: DNA
<213> ORGANISM: Artificial Sequence
<220> FEATURE:
<223> OTHER INFORMATION: variable domain of 2G4 heavy chain_optimized
      codon for CHO

<400> SEQUENCE: 24
caggtgcagc tggtggaatc tggtggcgga gttgtgcagc ctggcagatc cctgagactg    60
tcttgtgccg cctccggctt caccttctcc agatacggaa tgcactgggt ccgacaggcc   120
cctggcaaag gattggaatg ggtcgccgtg atttggtacg acggcaccaa caaggactac   180
accgactctg tgcggggcag attcaccatc tctcgggaca ctccaagaa cacccctgtac   240 ctgcagatga actccctgag agccgaggac accgccgtgt actactgtgc cagagaggat   300
tgggccgaag ccttcgatat gtggggccag ggcacaaccg tgaccgtgtc ctct         354

<210> SEQ ID NO 25
<211> LENGTH: 238
<212> TYPE: PRT
<213> ORGANISM: Artificial Sequence
<220> FEATURE:
<223> OTHER INFORMATION: 2G4 light chain

<400> SEQUENCE: 25

Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Leu Leu His Ser Asn Gly Tyr Asn Tyr Leu Asp Trp Tyr Leu Gln Lys
        50                  55                  60

Pro Gly Gln Ser Pro Gln Leu Leu Ile Tyr Leu Gly Ser Asn Arg Ala
65                  70                  75                  80
```

-continued

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Ile Thr Phe Gly Gln Gly Thr Arg Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 26
<211> LENGTH: 468
<212> TYPE: PRT
<213> ORGANISM: Artificial Sequence
<220> FEATURE:
<223> OTHER INFORMATION: 2G4 heavy chain

<400> SEQUENCE: 26

Met Glu Thr Asp Thr Leu Leu Leu Trp Val Leu Leu Leu Trp Val Pro
1               5                   10                  15

Gly Ser Thr Gly Gln Val Gln Leu Val Glu Ser Gly Gly Gly Val Val
            20                  25                  30

Gln Pro Gly Arg Ser Leu Arg Leu Ser Cys Ala Ala Ser Gly Phe Thr
        35                  40                  45

Phe Ser Arg Tyr Gly Met His Trp Val Arg Gln Ala Pro Gly Lys Gly
    50                  55                  60

Leu Glu Trp Val Ala Val Ile Trp Tyr Asp Gly Thr Asn Lys Asp Tyr
65                  70                  75                  80

Thr Asp Ser Val Arg Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Glu Asp Trp Ala Glu Ala Phe Asp Met Trp
        115                 120                 125

Gly Gln Gly Thr Thr Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 27
<211> LENGTH: 717
<212> TYPE: DNA
<213> ORGANISM: Artificial Sequence
<220> FEATURE:
<223> OTHER INFORMATION: 2G4 light chain

<400> SEQUENCE: 27
atggaaacag acacactcct cctctgggtc ctcctcctct gggtcccagg cagcacagga      60
gatattgtga tgactcagtc tccactctcc ctgcccgtca cccctggaga gccggcctcc     120
atctcctgca ggtctagtca gagcctcctg catagtaatg gatacaacta tttggattgg     180
tacctgcaga agccagggca gtctccacag ctcctgatct atttgggttc taatcgggcc     240
tccggggtcc ctgacaggtt cagtggcagt ggatcaggca cagattttac actgaaaatc     300
agcagagtgg aggctgagga tgttggggtt tattactgca tgcaagctct acaaactatc     360
accttcggcc aagggacacg actggagatt aaacgtacgg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540

| ggtaactccc aggagagtgt cacagagcag gacagcaagg acagcaccta cagcctcagc | 600 |
| agcaccctga cgctgagcaa agcagactac gagaaacaca agtctacgc ctgcgaagtc | 660 |
| acccatcagg gcctgagctc gcccgtcaca aagagcttca caggggaga gtgttga | 717 |

<210> SEQ ID NO 28
<211> LENGTH: 1407
<212> TYPE: DNA
<213> ORGANISM: Artificial Sequence
<220> FEATURE:
<223> OTHER INFORMATION: 2G4 heavy chain

<400> SEQUENCE: 28

| atggaaacag acacactcct cctctgggtc ctcctcctct gggtcccagg cagcacagga | 60 |
| caggtgcagc tggtggagtc tgggggaggc gtggtccagc ctgggaggtc cctgagactc | 120 |
| tcctgtgcag cgtctggatt caccttcagt cgctatggca tgcactgggt ccgccaggct | 180 |
| ccaggcaagg gctggagtg gtggcagtt atatggtatg atggaactaa taaagactat | 240 |
| acagactccg tgaggggccg attcaccatc tccagagaca attccaagaa cacgctgtat | 300 |
| cttcaaatga acagcctgag agccgaggac acggctgtgt attactgtgc gagagaagat | 360 |
| tgggctgagg cttttgatat gtggggccaa gggacaacgg tcaccgtctc ttcagcctcc | 420 |
| accaagggcc catcggtctt ccccctggca ccctcctcca agagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct gggcaccca gacctacatc | 660 |
| tgcaacgtga atcacaagcc cagcaacacc aaggtggaca gaaagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| acatgcgtgg tggtggacgt gagccacgaa gaccctgagg tcaagttcaa ctggtacgtg | 900 |
| gacggcgtgg aggtgcataa tgccaagaca agccgcggg aggagcagta caacagcacg | 960 |
| taccgtgtgg tcagcgtcct caccgtcctg caccaggact ggctgaatgg caaggagtac | 1020 |
| aagtgcaagg tcagcaacaa agccctccca gcccccatcg agaaaaccat ctccaaagcc | 1080 |
| aaagggcagc cccgagaacc acaggtgtac accctgcccc catcccggga tgagctgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctacagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg taaatga | 1407 |

<210> SEQ ID NO 29
<211> LENGTH: 717
<212> TYPE: DNA
<213> ORGANISM: Artificial Sequence
<220> FEATURE:
<223> OTHER INFORMATION: 2G4 light chain_optimized codon for CHO

<400> SEQUENCE: 29

| atggaaaccg acacactgct gctgtgggtg ctgctcttgt gggtgccagg atctaccggc | 60 |
| gacatcgtga tgacccagtc tccactgagc ctgcctgtga cacctggcga gcctgcttcc | 120 |

| | |
|---|---|
| atctcctgca gatcctctca gtccctgctg cactccaacg gctacaacta cctggactgg | 180 |
| tatctgcaga agcccggcca gtctcctcag ctgctgatct acctgggctc aacagagct | 240 |
| tctggcgtgc ccgatagatt ctccggctct ggctctggca ccgacttcac cctgaagatc | 300 |
| tccagagtgg aagccgagga cgtgggcgtg tactactgta tgcaggccct gcagaccatc | 360 |
| accttcggcc agggaaccag actggaaatc aagcggacag tggccgctcc ttccgtgttc | 420 |
| atcttcccac cttccgacga gcagctgaag tccggcacag cttctgtcgt gtgcctgctg | 480 |
| aacaacttct accctcggga agccaaggtg cagtggaagg tggacaatgc cctgcagtcc | 540 |
| ggcaactccc aagagtctgt gaccgagcag gactccaagg acagcaccta cagcctgtcc | 600 |
| tccacactga ccctgtccaa ggccgactac gagaagcaca aggtgtacgc ctgcgaagtg | 660 |
| acccatcagg gcctgtctag ccctgtgacc aagtctttca ccggggcga gtgctga | 717 |

<210> SEQ ID NO 30
<211> LENGTH: 1407
<212> TYPE: DNA
<213> ORGANISM: Artificial Sequence
<220> FEATURE:
<223> OTHER INFORMATION: 2G4 heavy chain_optimized codon for CHO

<400> SEQUENCE: 30

| | |
|---|---|
| atggaaaccg acacactgct gctgtgggtg ctgctcttgt gggtgccagg atctacagga | 60 |
| caggtgcagc tggtggaatc tggtggcgga gttgtgcagc ctggcagatc cctgagactg | 120 |
| tcttgtgccg cctccggctt caccttctcc agatacggaa tgcactgggt ccgacaggcc | 180 |
| cctggcaaag gattgaatg ggtcgccgtg atttggtacg acggcaccaa caaggactac | 240 |
| accgactctg tgcggggcag attcaccatc tctcgggaca actccaagaa caccctgtac | 300 |
| ctgcagatga actccctgag agccgaggac accgccgtgt actactgtgc cagagaggat | 360 |
| tgggccgaag ccttcgatat gtggggccag ggcacaaccg tgaccgtgtc ctctgcttct | 420 |
| accaagggac ccagcgtgtt ccctctggct ccttccagca gtctacctc tggcggaaca | 480 |
| gctgctctgg ctgcctggt caaggattac ttccctgagc ctgtgacagt gcctggaaac | 540 |
| tctggcgctc tgacatccgg cgtgcacacc tttccagctg tgctgcaatc ctccggcctg | 600 |
| tactctctgt cctccgtcgt gacagtgcct tccagctctc tgggaaccca gacctacatc | 660 |
| tgcaatgtga accacaagcc ttccaacacc aaggtggaca gaaggtgga cccaagtcc | 720 |
| tgcgacaaga cccacacctg tccaccatgt cctgctccag aactgctcgg cggaccttcc | 780 |
| gtgttcctgt tcctccaaa gcctaaggac accctgatga tctctcggac ccctgaagtg | 840 |
| acctgcgtgg tggtggatgt gtctcacgag gatcccgaag tgaagttcaa ttggtacgtg | 900 |
| gacggcgtgg aagtgcacaa cgccaagacc aagcctagag aggaacagta caactccacc | 960 |
| tacagagtgg tgtccgtgct gaccgtgctg caccaggatt ggctgaacgg caaagagtac | 1020 |
| aagtgcaagg tgtccaacaa ggccctgcct gctcctatcg aaaagaccat ctccaaggcc | 1080 |
| aagggccagc ctagggaacc ccaggtttac accttgcctc catctcggga cgagctgacc | 1140 |
| aagaaccagg tgtccctgac ctgtctcgtg aagggcttct accctccga tatcgccgtg | 1200 |
| gaatgggagt ctaatggcca gcctgagaac aactacaaga caccctcc tgtgctggac | 1260 |
| tccgacggct cattcttcct gtactccaag ctgacagtgg acaagtccag atggcagcag | 1320 |
| ggcaacgtgt tctctgctc cgtgatgcac gaggccctgc acaatcacta cacccagaag | 1380 |
| tccctgtctc tgagccccgg caaatga | 1407 |

ANTI-C-KIT ANTIBODY

CROSS REFERENCE TO RELATED APPLICATIONS

This application is a National Stage of International Application No. PCT/KR2019/013310 filed Oct. 10, 2019, claiming priority based on Korean Patent Application No. 10-2018-0120233 filed Oct. 10, 2018, the entire disclosures of which are incorporated herein by reference.

TECHNICAL FIELD

The present invention relates to a novel anti-C-KIT antibody or an antibody fragment thereof. In addition, the present invention relates to a composition for preventing or treating angiogenesis-related diseases comprising the anti-C-KIT antibody or an antibody fragment thereof, or a kit for diagnosing angiogenesis-related diseases.

BACKGROUND ART

Angiogenesis is a process through which new blood vessels form from pre-existing vessels. Abnormal or excessive angiogenesis may cause a variety of diseases. For example, angiogenesis is one of the causes of tumor growth as well as the development of tumor from benign to malignant, and the malignant transformation in a benign tumor, and excessive formations of new blood vessels have been reported in various disease, e.g. eye diseases such as age-related macular degeneration, diabetic retinopathy, glaucoma, rheumatoid arthritis, psoriasis, chronic inflammation (Cameliet and Jain, Nature, 407:249, 2000). For this reason, many studies have been conducted to treat angiogenesis-related diseases using angiogenesis inhibitors, and various angiogenesis promoting and inhibiting factors involved in angiogenesis processes such as growth, migration, differentiation of vascular endothelial cells were discovered.

Angiogenesis inhibitors may be classified into several categories comprising matrix-breakdown inhibitors, endothelial cell inhibitors, angiogenesis inhibitors depending on the mechanism of action. The angiogenesis inhibitors comprise drugs which target VEGFR2, VEGFR1, PDGFR, C-KIT, FLT3, etc. and suppress their activity, signaling, production, etc. C-KIT, one of the targets of the angiogenesis inhibitor, belongs to class III of receptor tyrosine kinase (RTK), and is also known as a receptor for SCF (Stem Cell Factor). The SCF is a cytokine that binds to the C-KIT receptor, and has been reported as an important role in the differentiation and production of blood cells, sperm, and melanocytes.

The SCF binds to and interacts with the ligand binding domain of C-KIT, and accordingly the C-KIT protein is phosphorylated to have an activity. It regulates various biological functions such as cell growth, differentiation and proliferation through the signaling processes such as PI3K/AKT system, RAS/MAP kinase. In particular, it has been reported on the action of SCF/C-KIT stimulation in angiogenesis (Angiogenesis in Health, Disease and Malignancy, pp 33-36).

As commercially available drugs targeting C-KIT, there are Gleevec (Imatinib mesylate) and Sutent (Sunitinib malate). However, these are multi-targeted treatments that inhibit several kinases, and therapeutic limitations such as many side effects, low specificity and bioavailability, antigenicity and inappropriate pharmacokinetics have been reported. Therefore, a development of an effective therapeutic agent that is specific to C-KIT and has no side effects for diseases related to angiogenesis by activation of C-KIT is required.

As a result of the inventors' efforts to find a therapeutic substance for angiogenesis-related diseases, it was confirmed that a particular anti-C-KIT antibody specifically binding to C-KIT can significantly inhibit angiogenesis and thus can have excellent therapeutic ability for angiogenesis-related diseases, and the present invention has been completed.

TECHNICAL PROBLEM

One purpose of the present invention is to provide an anti-C-KIT antibody or antibody fragment thereof having an excellent C-KIT inhibitory ability by specifically binding to domain II of the C-KIT protein. Another purpose of the present invention is to provide a composition for preventing or treating angiogenesis-related diseases and a diagnostic kit, comprising the anti-C-KIT antibody or antibody fragment thereof.

TECHNICAL SOLUTION

According to one aspect of the present invention, the present invention provides an anti-C-KIT antibody or antibody fragment thereof that specifically binds to C-KIT.

According to one aspect of the present invention, the anti-C-KIT antibody or antibody fragment thereof according to the present invention specifically binds to domain II of C-KIT.

The term "antibody" as used herein refers to an immunoglobulin molecule having immunological reactivity with a specific antigen, or a protein molecule serving as a receptor for specifically recognizing an antigen. Accordingly, in the present invention, "antibody" is used in a broad sense, and is interpreted to include polyclonal antibody, monoclonal antibody, whole antibody (antibody consisting of at least two heavy chains and two light chains linked by disulfide bonds) and antibody fragments. The whole antibody includes IgA, IgD, IgE, IgM and IgG. In addition, the IgG may comprise IgG1, IgG2, IgG3, and IgG4 as subtypes.

The term "antibody fragment" as used herein refers to an antigen-binding fragment or analog of an antibody which retains some of the binding specificity of the parent antibody and comprises a portion (for example, one or more CDRs) or variable region of the antigen binding region of the parent antibody. The antibody fragment is, for example, Fab, Fab', F(ab')2, Fv fragment, sc-Fv, unibody, diabody, linear antibody, nanobody, domain antibody, or multispecific antibody fragment formed from the antibody fragment.

The term "heavy chain" as used herein refers to a whole heavy chain comprising a heavy chain variable region and a heavy chain constant region, and fragment thereof. In the heavy chain, there are types of gamma (γ), mu (μ), alpha (α), delta (δ) and epsilon (ε).

The term "light chain" as used herein refers to a whole light chain comprising a light chain variable region and a light chain constant region, and fragment thereof. In the light chain, there are types of kappa (κ) and lambda (λ).

In the present invention, the antibody is a whole antibody or an antibody fragment having antigen-binding ability. The heavy chain may be any one of gamma (γ), mu (μ), alpha (α), delta (δ) or epsilon (ε) type, and the light chain may be kappa (κ) or lambda (λ) type. According to one aspect of the invention, the light chain is kappa type.

The term "C-KIT" as used herein belongs to class III of receptor tyrosine kinase (RTK), and is also known as a receptor of SCF.

C-KIT, one of the targets of the angiogenesis inhibitor, belongs to class III of receptor tyrosine kinase (RTK), and is a receptor of SCF (Stem Cell Factor) that plays an important role in hematopoiesis.

The term "anti-C-KIT antibody" as used herein refers to an antibody that specifically binds to C-KIT. The anti-C-KIT antibody specifically binds to domain II of C-KIT, thereby the activity or activation of C-KIT can be inhibited or neutralized.

According to another aspect of the present invention, the anti-C-KIT antibody or antibody fragment thereof according to the present invention comprises a light chain variable region comprising a light chain CDR1 represented by SEQ ID NO: 1, a light chain CDR2 represented by SEQ ID NO: 2, and a light chain CDR3 represented by SEQ ID NO: 3.

According to another aspect of the present invention, the anti-C-KIT antibody or antibody fragment thereof according to the present invention comprises a heavy chain variable region comprising a heavy chain CDR1 represented by SEQ ID NO: 4, a heavy chain CDR2 represented by SEQ ID NO: 5, and a heavy chain CDR3 represented by SEQ ID NO: 6.

According to another aspect of the present invention, a light chain variable region of the anti-C-KIT antibody or antibody fragment thereof according to the present invention comprises the amino acid sequence of SEQ ID NO: 7.

According to another aspect of the present invention, a heavy chain variable region of the anti-C-KIT antibody or antibody fragment thereof according to the present invention comprises the amino acid sequence of SEQ ID NO: 8.

According to another aspect of the present invention, the anti-C-KIT antibody or antibody fragment thereof according to the present invention may comprise a light chain comprising the amino acid sequence of SEQ ID NO: 25.

According to another aspect of the present invention, the anti-C-KIT antibody or antibody fragment thereof according to the present invention may comprise a heavy chain comprising the amino acid sequence of SEQ ID NO: 26.

The term "CDR (complementarity determining region)" as used herein refers to amino acid sequence of hypervariable region that forms an antigen-binding site as part of the variable region of an antibody produced by B cells and T cells. The amino acid sequence of the heavy chain comprises three non-contiguous CDRs: heavy chain $CDR_{H1}$, $CDR_{H2}$, $CDR_{H3}$ and the amino acid sequence of the light chain comprises three non-contiguous CDRs: light chain $CDR_{L1}$, $CDR_{L2}$, $CDR_{L3}$. The CDR is a region concerned with antigen recognition and plays a crucial role in the diversity of antigen specificity by providing major contact residues in binding of an antibody to an antigen or epitope.

The antibody or antibody fragment thereof according to the present invention comprises a sequence that shows substantial identity to the sequence described in the sequence list. The substantial identity means that the two sequences are aligned to correspond as much as possible and analyzed using an algorithm commonly used in the art, and then show homology between sequences of 80%, 90%, 95% or more.

In addition, the anti-C-KIT antibody of the present invention comprises not only the sequence of the anti-C-KIT antibody described herein, but also a biological equivalent thereof within a range of specifically recognizing and binding C-KIT. For example, it may comprise additional mutations in the sequence to improve antibody binding affinity and/or biological properties, and it may comprise additional mutations within a range that does not alter the overall activity of the molecule.

According to another aspect of the present invention, the anti-C-KIT antibody or antibody fragment thereof may comprise a constant region derived from human IgG1. According to one aspect of the present invention, the present invention provides a human anti-C-KIT antibody comprising the light chain variable region, the heavy chain variable region and the human IgG1-derived constant region.

The term "human antibody" as used herein refers to an antibody in which the framework and CDR regions have variable regions derived from human immunoglobulin sequences. Human antibodies in the present invention may comprise amino acid residues that are not encoded by human-derived immunoglobulin sequences (e.g., mutations introduced by random or site-specific mutagenesis in vitro or by somatic mutation in vivo). The human antibody may be in the form of a whole antibody or a form comprising a functional fragment of an antibody molecule. Since all components of the human antibody are derived from humans, the probability of an immune response occurring when administered to a human is less than that of a humanized antibody or a mouse antibody. Therefore, it has an advantage as a therapeutic antibody for human.

As a result of confirming the effect related to the angiogenesis inhibitory effect through various examples described below, the anti-C-KIT antibody or antibody fragment thereof according to the present invention can effectively prevent or treat angiogenesis-related diseases by significantly inhibiting angiogenesis.

According to another aspect of the present invention, the present invention provides a nucleic acid encoding an anti-C-KIT antibody or antibody fragment thereof.

The nucleic acid encoding the anti-C-KIT antibody or antibody fragment thereof according to the present invention may comprise the nucleotide sequences of SEQ ID NO: 9, SEQ ID NO: 10, and SEQ ID NO: 11. The nucleotide sequences of SEQ ID NO: 9, SEQ ID NO: 10, and SEQ ID NO: 11 encode light chain CDR1 represented by SEQ ID NO: 1, light chain CDR2 represented by SEQ ID NO: 2, and light chain CDR3 represented by SEQ ID NO: 3, respectively. The nucleotide sequences of SEQ ID NO: 9 to 11 may be codon-optimized for CHO cell respectively, and the nucleic acid comprising the codon-optimized nucleotide sequence should be construed to be included in the scope of a nucleic acid encoding the anti-C-KIT antibody or antibody fragment thereof according to the present invention. For example, the nucleic acid encoding the anti-C-KIT antibody or antibody fragment thereof according to the present invention may comprise SEQ ID NO: 17. SEQ ID NO: 18 and SEQ ID NO: 19.

Optionally, a nucleic acid encoding the anti-C-KIT antibody or antibody fragment thereof according to the invention may comprise the nucleotide sequences of SEQ ID NO: 12, SEQ ID NO: 13 and SEQ ID NO: 14. The nucleotide sequences of SEQ ID NO: 12, SEQ ID NO: 13, and SEQ ID NO: 14 encode heavy chain CDR1 represented by SEQ ID NO: 4, heavy chain CDR2 represented by SEQ ID NO: 5, and heavy chain CDR3 represented by SEQ ID NO: 6, respectively. The nucleotide sequences of SEQ ID NO: 12 to 14 may be codon-optimized for CHO cells respectively, and the nucleic acid comprising the codon-optimized nucleotide sequence should be construed to be included in the scope of a nucleic acid encoding the anti-C-KIT antibody or antibody fragment thereof according to the present invention. For example, the nucleic acids encoding the anti-C-KIT antibody or antibody fragment thereof according to the present invention may comprise SEQ ID NO: 20, 21 and 22.

According to one aspect of the present invention, the nucleic acid encoding the anti-C-KIT antibody or antibody fragment thereof according to the present invention may comprise a light chain variable region encoding nucleic acid comprising SEQ ID NO: 15 or 23.

According to another aspect of the present invention, the nucleic acid encoding the anti-C-KIT antibody or antibody fragment thereof according to the present invention may comprise a heavy chain variable region encoding nucleic acid comprising SEQ ID NO: 16 or 24.

According to another aspect of the present invention, the nucleic acid encoding the anti-C-KIT antibody or antibody fragment thereof according to the present invention may comprise a light chain encoding nucleic acid comprising SEQ ID NO: 27 or 29.

According to another aspect of the present invention, the nucleic acid encoding the anti-C-KIT antibody or antibody fragment thereof according to the present invention may comprise a heavy chain encoding nucleic acid comprising SEQ ID NO: 28 or 30.

The term "nucleic acid" as used herein comprises comprehensively DNA (gDNA and cDNA) and RNA. The nucleotides that make up the basic structural unit in a nucleic acid molecule comprise natural nucleotides as well as analogue nucleotides with modified sugar or base sites (Scheit, Nucleotide Analogs, John Wiley, New York (1980): Uhlman and Pevman, Chemical Review, 90:543-584 (1990)).

The nucleic acid molecule encoding the anti-C-KIT antibody or antibody fragment thereof according to the present invention comprises a nucleotide sequence indicating substantial identity to the above-mentioned nucleotide sequences. The substantial identity means that the two sequences are aligned to correspond as much as possible and analyzed using an algorithm commonly used in the art, and then show homology between sequences of 80%, 90%, 95% or more.

According to another aspect of the present invention, the present invention provides a vector comprising the nucleic acid and a cell transformed with the vector.

The term "vector" as used herein refers to any one that can be inserted into a host cell and capable of gene replication. The vector includes plasmid, linear nucleic acid, cosmid, RNA vector, viral vector, etc., and the viral vector comprises, but is not limited to, retrovirus, adenovirus, adeno-associated virus, and the like. A recombinant vector system of the present invention can be constructed through various methods known in the art. In addition, the vector of the present invention can be constructed as a vector for cloning or expression, and can be constructed using prokaryotic or eukaryotic cells as a host.

Furthermore, the cells may be prokarvotic cells, eukarvotic cells or animal cells. An appropriately selected host cell can be transformed with the vector and it may be used to express and/or secrete a target protein. The host cells may be immortalized hybridoma cells, N/SO myeloma cells, 293 cells, HuT 78 cells, CHO cells, HELA cells, COS cells, and the like, preferably CHO cells. However, the present invention is not limited thereto, and any host cell known in the art can be used as the host cell of the present invention.

According to another aspect of the present invention, the present invention provides a pharmaceutical composition for preventing or treating angiogenesis-related diseases comprising an anti-C-KIT antibody or antibody fragment thereof.

According to another aspect of the present invention, the present invention provides a method for treating or preventing angiogenesis-related diseases in a subject, comprising administering an anti-C-KIT antibody or antibody fragment thereof or a composition comprising the same to the subject in need thereof.

The term "treatment" as used herein comprises that the symptoms of angiogenesis-related diseases are improved, reversed or cured by administering the composition according to the present invention.

The term "prevention" as used herein comprises any reduction, delay, or block of the occurrence or recurrence of angiogenesis-related diseases by administering the composition according to the present invention.

The term "angiogenesis-related disease" as used herein comprises a disease caused by angiogenesis. These include cancer, leukemia, ophthalmic vascular diseases, rheumatoid arthritis, psoriasis, chronic wounds, chronic inflammation, hemangioma, hemangiofibroma, vascular malformations, arteriosclerosis, vascular adhesions, vasculitis, pyogenic granuloma, blister diseases, pulmonary hypertension, asthma, nasal polyps, infectious diseases, inflammatory bowel disease, periodontal disease, peritoneal adhesions, endometriosis, uterine bleeding, ovarian cysts, osteomyelitis, osteitis, sepsis and autoimmune diseases, and the like. Preferably, it may be cancer and ophthalmic vascular diseases, but it is not limited thereto.

The cancer may be bone cancer, lung cancer, brain cancer, neck cancer, thyroid cancer, parathyroid cancer, non-small cell lung cancer, gastric cancer, liver cancer, pancreatic cancer, skin cancer, intradermal or intraocular melanoma, rectal cancer, anal cancer, colon cancer, uterine cancer, ovarian cancer, fallopian tube carcinoma, endometrial carcinoma, cervical carcinoma, vaginal carcinoma, vulvar carcinoma, Hodgkin's disease, esophageal cancer, small intestine cancer, endocrine adenocarcinoma, adrenal cancer, soft tissue sarcoma, urethral cancer, penile cancer, prostate cancer, bladder cancer, kidney cancer, or ureteral cancer, renal cell carcinoma, renal pelvic carcinoma, central nervous system tumor, central nervous system lymphoma, spinal cord tumor, glioblastoma, brain stem glioma, or pituitary adenoma.

The ophthalmic vascular diseases may be diabetic retinopathy, macular degeneration, senile macular degeneration, glaucoma, glaucoma-related retinal pigment degeneration, choroidal neovascularization, retinopathy of prematurity, corneal dystrophy or retinoschisis.

The pharmaceutical composition according to the present invention may contain the anti-C-KIT antibody or fragment thereof alone, or may further contain one or more pharmaceutically acceptable carriers, excipients, or diluents.

The pharmaceutically acceptable carrier may further comprise, for example, a carrier for oral administration or a carrier for parenteral administration. Carriers for oral administration may comprise lactose, starch, cellulose derivatives, magnesium stearate, stearic acid, and the like. In addition, the carrier for parenteral administration may comprise water, suitable oil, saline, aqueous glucose and glycol, and the like, and may further comprise a stabilizer and a preservative. Examples of stabilizers include antioxidants such as sodium hydrogen sulfite, sodium sulfite or ascorbic acid. Examples of preservatives may be benzalkonium chloride, methyl- or propyl-paraben and chlorobutanol. As other pharmaceutically acceptable carriers, those known in the art may be used (Remington's Pharmaceutical Sciences, 19th ed. Mack Publishing Company, Easton, PA, 1995).

The pharmaceutical composition of the present invention can be administered to mammals comprising humans by any method. For example, it can be administered orally or parenterally. As a parenteral administration method, intravenous, intramuscular, intraarterial, intramedullary, intrathecal, intracardiac, transdermal, subcutaneous, intraperitoneal, intranasal, intestinal, topical, sublingual or rectal administration may be used, and are not limited thereto. For example, the pharmaceutical composition of the present invention may be prepared in an injection form and administered by a method of lightly pricking the skin with a 30-gauge thin injection needle, or by applying it directly to the skin.

The pharmaceutical composition of the present invention can be formulated as a formulation for oral administration or parenteral administration according to the route of administration as described above. In the case of a formulation for oral administration, the composition of the present invention may be formulated using a method known in the art as a powder, granule, tablet, pill, dragee, capsule, liquid, gel, syrup, slurry, suspension, etc. For example, as oral preparations, tablets or dragees can be obtained by mixing the active ingredient with a solid excipient, pulverizing it, adding a suitable auxiliary agent, and processing into a granule mixture. Examples of excipients comprise sugars comprising lactose, dextrose, sucrose, sorbitol, mannitol, xylitol, erythritol and maltitol, and starches comprising corn starch, wheat starch, rice starch and potato starch, and cellulose comprising cellulose, methyl cellulose, sodium carboxymethylcellulose, and hydroxy propylmethyl-cellulose, and fillers such as gelatin, polyvinylpyrrolidone, and like. In addition, in some cases, cross-linked polyvinylpyrrolidone, agar, alginic acid or sodium alginate may be added as a disintegrant. In addition, the pharmaceutical composition of the present invention may further comprise an anti-aggregating agent, a lubricant, a wetting agent, a fragrance, an emulsifying agent and a preservative. In the case of a formulation for parenteral administration, it can be formulated in the form of injections, creams, lotions, ointments for external use, oils, moisturizers, gels, aerosols, and nasal inhalants by a method known in the art. These formulations are described in documents generally known in all pharmaceutical chemistry fields (Remington's Pharmaceutical Science, 15th Edition, 1975 Mack Publishing Company, Easton, Pennsylvania 18042, Chapter 87: Blaug, Seymour).

The total effective amount of the pharmaceutical composition of the present invention may be administered to a patient in a single dose, and may be administered by a fractionated treatment protocol with multiple doses for a long period of time. The pharmaceutical composition of the present invention may vary the content of the active ingredient depending on the degree of symptoms of the disease. For example, the daily dosage of the pharmaceutical composition of the present invention may be 0.0001 to 100 mg/kg. However, the dosage of the pharmaceutical composition of the present invention may be determined in consideration of various factors such as age, weight, health condition, sex, disease severity, diet, excretion rate, route of administration, frequency of treatment, and one of ordinary skill in the art will be able to determine the appropriate effective dosage. The pharmaceutical composition according to the present invention is not particularly limited in its formulation, route of administration, and method of administration as long as it shows the effects of the present invention.

In addition, the pharmaceutical composition of the present invention may be administered as an individual therapeutic agent or administered in combination with other therapeutic agents. When administered in combination with other therapeutic agents, the composition of the present invention and the other therapeutic agents may be administered simultaneously, individually or sequentially. The other therapeutic agent may be a substance already known to have an effect of treating or improving angiogenesis-related diseases, and comprises all other anticancer therapies comprising non-pharmacological therapy such as radiation therapy.

When the pharmaceutical composition of the present invention is administered in combination with other therapeutic agents, the anti-C-KIT antibody contained in the composition of the present invention and other therapeutic agents are separately formulated into separate containers or formulated together in the same container.

According to another aspect of the present invention, the present invention provides a kit for diagnosing angiogenesis-related diseases comprising an anti-C-KIT antibody or antibody fragment thereof.

The term "biological sample" as used herein comprises tissue, cells, blood, serum, plasma, tissue autopsy samples (brain, skin, lymph nodes, spinal cord), and the like, but is not limited thereto.

By reacting the antibody of the present invention with a biological sample, the onset or possibility of angiogenesis-related disease can be diagnosed. Specifically, it can be diagnosed by contacting an anti-C-KIT antibody or a functional fragment thereof with a biological sample and confirming the formation of an antigen-antibody complex. Since the diagnostic kit of the present invention contains an antibody, it can be made to be suitable for various immunoassays or immunostaining. The immunoassay or immunostaining may be enzymatic immunoassay (ELISA), immunofluorescence, Western blotting, immunohistochemistry staining, flow cytometry, immunocytochemistry, radioimmunoassay (RIA), protein chip, and the like, but it is not limited thereto.

Labels for qualitatively or quantitatively determining the formation of an antigen-antibody complex comprise enzymes, fluorescent substances, ligands, luminescent substances, microparticle, redox molecules, and radioisotopes, but are not limited thereto.

The novel anti-C-KIT antibody or antibody fragment thereof according to the present invention specifically binds to a particular domain II of C-KIT and has a strong affinity. Accordingly, the antibody or antibody fragment thereof according to the present invention has a very excellent effect of significantly inhibiting the generation of abnormal or excessive neovascularization, and can effectively prevent or treat angiogenesis-related diseases. In addition, the antibody or antibody fragment thereof according to the present invention can be effectively used in the study of angiogenesis-related diseases because it has cross-reactivity with mice and rats in addition to human.

BRIEF DESCRIPTION OF FIGURES

FIG. 6 shows the nucleotide sequence, amino acid sequence, and CDR region of the light chain variable region of the 2G4 antibody (SEQ ID NOS: 7 and 15).

FIG. 7 shows the nucleotide sequence, amino acid sequence, and CDR region of the heavy chain variable region of the 2G4 antibody (SEQ ID NOS: 8 and 16).

FIG. 9 is a graph showing the analysis results of SPR for confirming the C-KIT affinity of 2G4 antibody.

EXAMPLES

Figure 1:
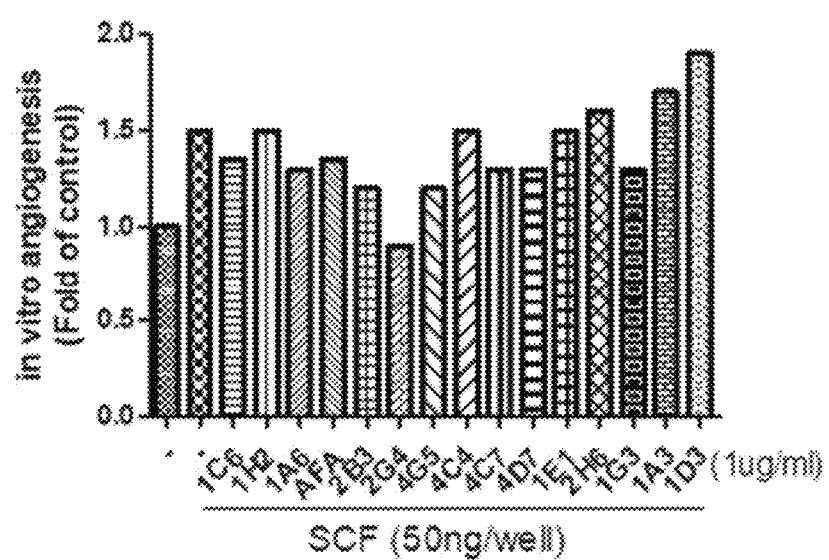
FIG. 1 is a graph showing the tube formation inhibitory effect of a total of fifteen anti-C-KIT monoclonal antibodies in a relative level compared to the non-treated control group when HUVEC cells were treated with SCF.

In the following, exemplary embodiments of the inventive concept will be explained in further detail with reference to examples. However, the following examples are meant to exemplify the present invention, and the scope of the invention is not restricted by these examples. Terms that are not specifically defined in the present specification should be understood as having meanings commonly used in the technical field to which the present invention belongs.

Example 1. C-KIT Antibody Production Cell Line Preparation 1-1. Preparation of Immunized Mice An emulsion was prepared by mixing 50 μg (based on one mouse) of recombinant C-KIT protein (cat #PKSH030939) purchased from Elabscience with the same volume of complete Freund's Adjuvant (sigma, USA). The prepared emulsion was injected intraperitoneally into six humanized NSG mice prepared by injection of 7-week-old female human CD34+ cells. 50 μg of antigen was injected into each mouse in a total volume of 500 μl. After 1 week and 2 weeks, an emulsion prepared by mixing an incomplete Freund's Adjuvant (sigma, USA) with an antigen was further injected into the intraperitoneal cavity of the mouse, respectively.

1-2. Antibody Production Confirmation

Blood was collected from the eyeballs of mice immunized through the above method, placed in a 1.5 ml microcentrifuge tube, and centrifuged at 13,000 rpm for 10 minutes. Serum was separated and stored at −20° C. until an experiment to confirm antibody production is performed. After confirming the antibody production by carrying out an enzyme immunoassay method using an antigenic protein, an emulsion in which an antigen was mixed with an incomplete Freund's Adjuvant (Sigma, USA) was further injected into the intraperitoneal cavity of the mouse 3 days before cell fusion.

1-3. Preparation of Hybridomas

After confirming the antibody production, the mice were sacrificed. The splenocytes were isolated and fused with myeloma cells P3X63Ag 8.653 (ATCC CRL-1580) to prepare hybridomas.

Specifically, P3X63Ag 8.653 cells of mice were cultured in a culture plate using RPMI1640 medium supplemented with 10% fetal bovine serum. To perform cell fusion, P3X63Ag 8.653 cells were washed twice with serum-free RPMI640 medium (Hyclone, USA), and adjusted to a cell concentration of 1×10$^7$. The mice were sacrificed by cervical dislocation, and the spleen was collected, and then placed in a mesh container (Sigma, USA) to separate cells. After preparing a suspension of splenocytes, the suspension was washed by centrifugation. Red blood cells were lysed by exposing the splenocyte solution to Tris-NH$_4$Cl (TRIS 20.6 g/L, NH$_4$Cl 8.3 g/L). Completely isolated antibody-producing cells were centrifuged at 400×g for 5 minutes. After that, it was washed twice in serum-free medium and resuspended in 10 ml medium. Lymphocytes were counted using a hemocytometer, and 1×10$^8$ lymphocytes were mixed with 1×10 P3X63Ag 8.653 cells (10:1) in serum-free medium.

After centrifugation at 400×g for 5 minutes, 1 ml of a solution was added dropwise using 50% (MN) polyethylene glycol 1500 (sigma, USA) heated at 37° C. and mixed for 1 minute. The fusion mixture solution thus prepared was diluted with serum-free RPMI1640 and centrifuged at 400×g for 3 minutes. Cells were suspended in 35 ml of RPMI1640 selective medium supplemented with 20% fetal bovine serum and HAT (100 μM hypoxanthine, 0.4 μM aminopterin, 16 μM thymidine). 100 μl of the suspension was loaded onto a 96-well plate coated with feeder cells (macrophages isolated from the peritoneal cavity using RPMI1640) one day before, and cultured at 37° C. 5% CO$_2$. After 5 days, the HAT medium was changed every 2-3 days, and the cells were cultured for 14 days. After 14 days, the secondary culture was performed by replacing with RPMI1640 medium supplemented with 20% fetal bovine serum and HT (a medium in which 0.4 μM aminopterin was removed from HAT).

1-4. Selection and Isolation of Antibody-Producing Fusion Cells

The supernatant of the previously prepared fusion cells culture medium was collected and subjected to an enzyme immunoassay to determine whether specific antibodies for the prepared antigen were produced or not. A culture medium of fusion cells exhibiting an appropriate concentration of 4 times or more compared to the negative control group was selected and transferred to a 24-well plate for culture. In addition, after culturing by dilution to contain one cell per well in a 96-well plate (limiting dilution), the culture solution was recovered, and the C-KIT protein used as an antigen was coated at 0.1 μg per well on a 96-well plate. After that, enzyme immunoassay is performed to finally select fusion cells producing 15 monoclonal antibodies (1C6, 1H2, 1A6, AFA, 2B3, 2G4, 4G5, 4C4, 4C7, 4D7, 1E1, 2H6, 1G3, 1A3, 1D3).

Example 2. C-KIT Antibody Selection

2-1. Tube Formation Analysis Using HUVEC

After dispensing 300 μl of Matriegel (Corning, USA) into a 24-well plate, HUVECs (Human Umbilical Vein Endothelial Cells) was dispensed into Matrigel with SCF (50 ng/ml) or SCF (50 ng/ml)+anti-C-KIT antibody (1 μg/ml). Thereafter, tube formation of HUVEC was observed, and the results are shown in FIG. 1.

In FIG. 1, according to the results of in vitro angiogenesis using HUVEC, it was confirmed that 2G4 is the most potent among 15 antibodies to inhibit HUVEC tube formation induced by SCF. This suggests that an anti-C-KIT antibody, referred to as 2G4, can be effectively used in the prevention or treatment of angiogenesis-related diseases.

2-2. Angiogenesis Inhibitory Effects Depending on the Concentrations of the 2G4 Antibody After dispensing 300 μl of Matrigel (Corning, USA) into a 24-well plate, HUVEC was dispensed into Matrigel with SCF (50 ng/ml), SCF (50 ng/ml)+2G4 antibody (0.1 μg/ml) or SCF (50 ng/ml)+2G4 antibody (I μg/ml). Thereafter, tube formation of HUVEC was observed, and the results are shown in FIG. 2.

Figure 2:
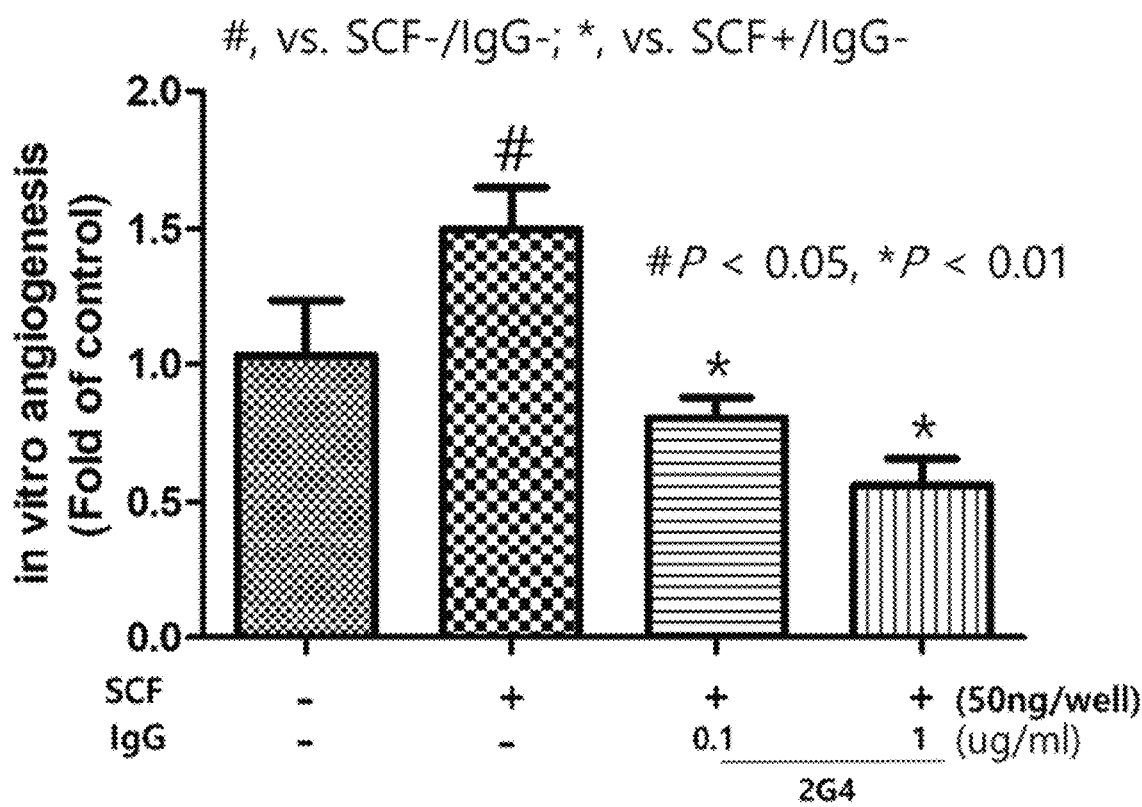
FIG. 2 is a graph showing the tube formation inhibitory effect by concentration of 2G4 antibody in a relative level compared to the non-treated control group when HUVEC cells were treated with SCF.

In FIG. 2, according to the results of tube formation analysis using HUVEC, it was confirmed that the 2G4 antibody inhibited HUVEC tube formation in a concentration-dependent manner. In particular, the 2G4 antibody was excellent in the ability to inhibit angiogenesis even at a concentration of 0.1 μg/ml.

2-3. Cross-Reaction Test on Mice

In order to test the cross-reactivity of the 2G4 antibody on mice, it was carried out in the same manner as in Example 2-2 using the mouse-derived endothelial cells MS-1.

Figure 3:
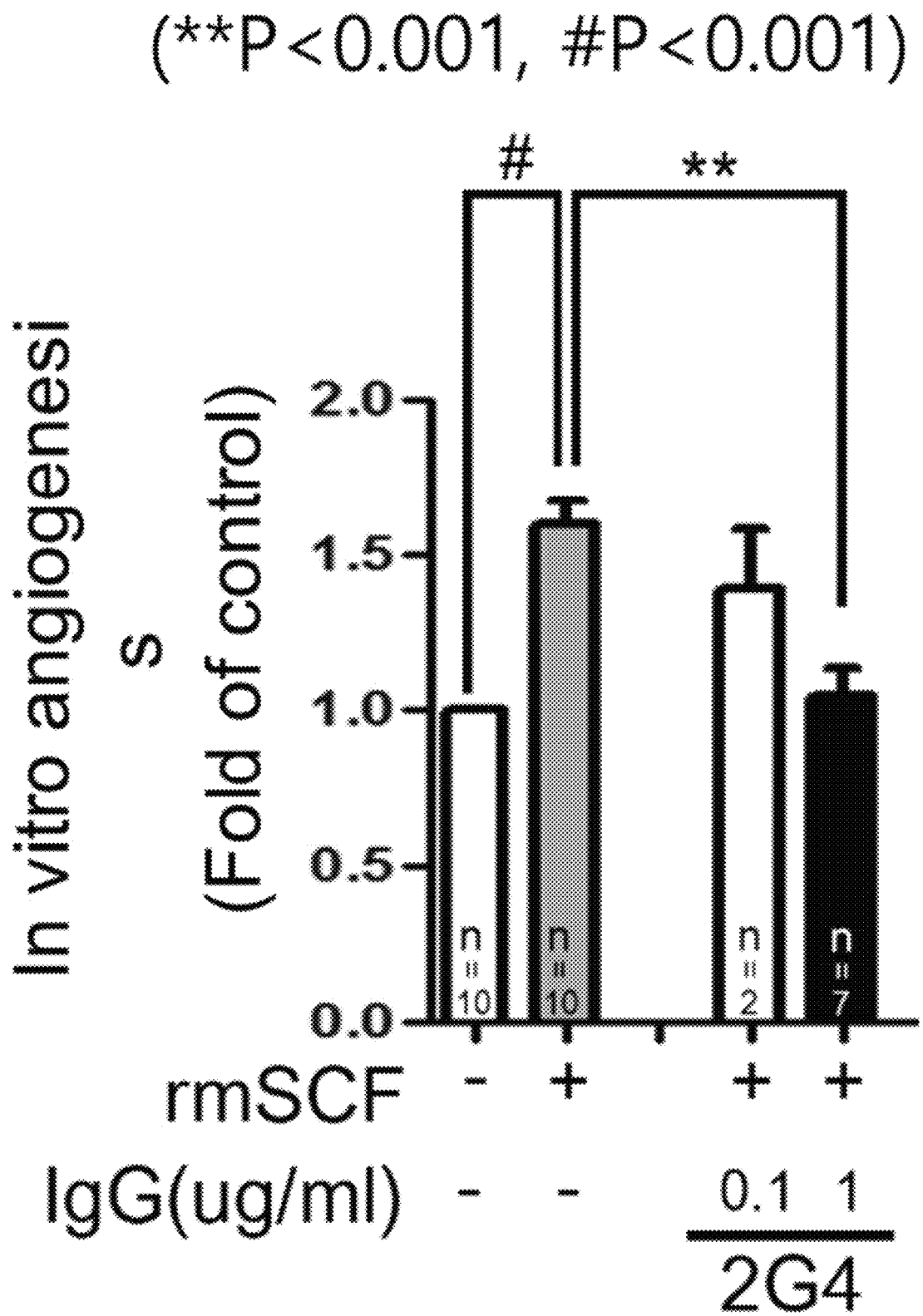
FIG. 3 is a graph showing the tube formation inhibitory effect by concentration of 2G4 antibody when mouse-derived endothelial cell MS-1 were treated with SCF.

As a result, as shown in FIG. 3, it was confirmed that the 2G4 antibody significantly inhibited angiogenesis of the mouse endothelial cells in the mouse-derived endothelial cells MS-1.

Figure 4:
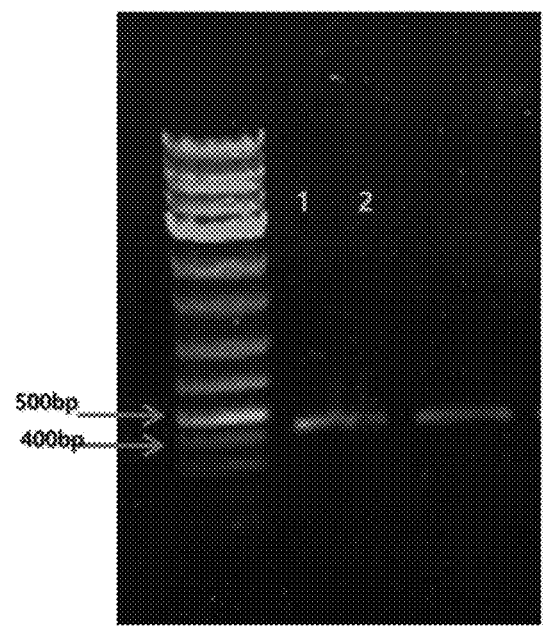
FIGS. 4 and 5 show the bands of the light chain variable region and the heavy chain variable region of the 2G4 antibody, respectively.

Example 3. Nucleotide Sequence Analysis of Anti-C-KIT Antibody IgG Variable Region Total RNA was isolated from the fusion cell 2G4 clone $5 \times 10^5$ obtained from Examples 1 and 2. cDNA was synthesized using random primer (bioneer, Korea) and reverse transcriptase. The kappa light chain domain was amplified from the cDNA using PROGEN's human IgG library primer set. The amplified nucleic acid was confirmed by agarose gel electrophoresis, and the results are shown in FIG. 4. Similarly, the heavy chain domain was amplified using PROGEN's human IgG library primer set and the results are shown in FIG. 5.

Figure 5:
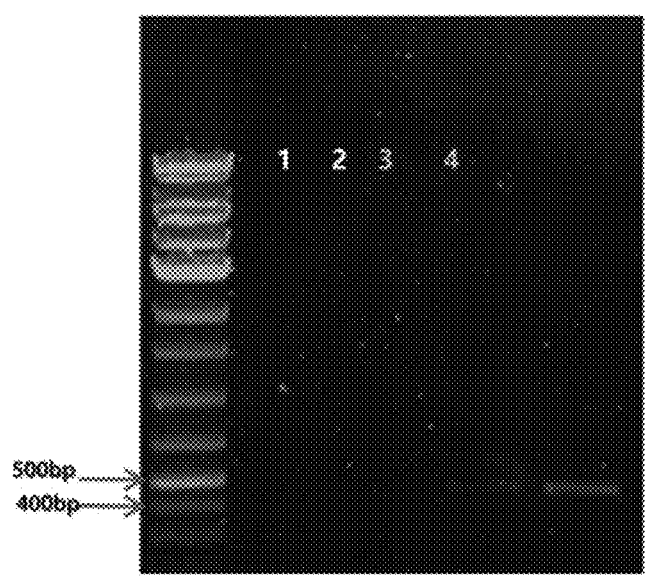

As shown in FIGS. 4 and 5, a band was found between the kappa light chain domain (414 bp) and the heavy chain domain (483 bp), confirming that a PCR product of the expected size was generated.

Thereafter, the PCR product was spread on an agarose gel, the band was cut, the agarose gel was dissolved at 60° C., and then the nucleic acid was purified using a spin column (Qiagen). The purified nucleic acid was cloned into a TOPO-TA vector, transformed into E. coli DH5a to obtain colonies, and then the obtained colonies were cultured to extract plasmids. Subsequently, PCR was performed again to obtain four plasmids, and then the nucleotide sequence of the 2G4 antibody was analyzed.

FIG. 6 shows the amino acid sequence and nucleotide sequence of the light chain variable region of the 2G4 antibody, which respectively correspond to the amino acid sequence of SEQ ID NO: 7 and the nucleotide sequence of SEQ ID NO: 15 in the sequence list attached to the present specification. In addition, CDR1, CDR2, and CDR3 of the light chain variable region in FIG. 6 are indicated in order in red, which correspond to the amino acid sequences of SEQ ID NOs: 1 to 3 and nucleotide sequences of SEQ ID NOs: 9 to 11, respectively, in the sequence list attached to the present specification.

FIG. 7 shows the amino acid sequence and nucleotide sequence of the heavy chain variable region of the 2G4 antibody, which respectively correspond to the amino acid sequence of SEQ ID NO: 8 and the nucleotide sequence of SEQ ID NO: 16 in the sequence list attached to the present specification. In addition, CDR1. CDR2, and CDR3 of the heavy chain variable region in FIG. 7 are indicated in order in red, which correspond to the amino acid sequences of SEQ ID NOs: 4 to 6 and nucleotide sequences of SEQ ID NOs: 12 to 14, respectively, in the sequence list attached to the present specification.

Example 4. Preparation of Anti-C-KIT Antibody

4-1. Fully Humanized Antibody Cloning

The variable region of the 2G4 antibody obtained in Example 3 was grafted onto a human Fc amino acid sequence, and cloned into a pCHO vector (lifetechnology).

The light chain variable region was fused in the frame for the human kappa constant region, and the heavy chain variable region was fused in the frame for the human IgG1 constant region.

A leader peptide sequence for secretion of the whole IgG1 antibody in the medium was added to the two genes to synthesize the gene, and then again verified through sequencing. Three clones were selected for the expression test in CHO cells. Glycerol stocks were prepared for the three clones, and a plasmid without endotoxin was prepared for the expression test in CHO cells.

4-2. Isolation and Purification of Antibody

The plasmid DNA obtained above was transfected into CHO-S cells. One week before transfection, CHO-S cells (Invitrogen, 10743-029) were transferred into monolayer cultures in the presence of DMEM supplemented with serum. After the cells were dispensed 1 day before transfection, a nucleic acid-lipofectamine complex was prepared for the transfection sample, and the cells were incubated overnight at 5% $CO_2$ and 37° C. in an incubator. The medium was incubated for a week while being added once every 2-3 days. Then, the culture solution was recovered, bonded to Protein A/G agarose (Invitrogen), and washed with PBS. Then, after eluting with 0.1 M glycine (pH 2.8), it was neutralized with 1 M Tris-HCl (pH 8.0). After dialysis with PBS, it was stored at −70° C.

Figure 8:
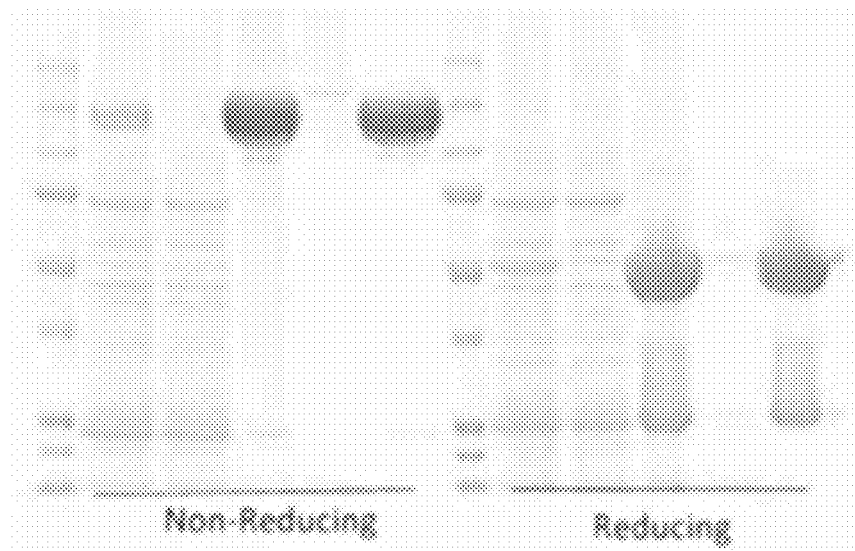
FIG. 8 shows the analysis results of SDS-PAGE of 2G4 antibodies obtained through cloning, separation and purification.

The separated and purified 2G4 antibody was running on 6% SDS-PAGE under Non-reducing and Reducing conditions to confirm the purity and size of the antibody. The results are shown in FIG. 8. As shown in FIG. 8, a 50 kDa heavy chain and a 25 kDa light chain band were observed as a result of SDS-PAGE, confirming that the antibody was accurately produced.

Example 5. Affinity of 2G4 Antibody

In order to confirm the C-KIT binding ability of the 2G4 antibody, SPR (Surface Plasmon Resonance) was performed. Using SR7500DC (Reichert, USA), 20 μg of human C-KIT (elabscience, PKSH030939) used for antibody preparation. 20 μg of mouse C-KIT (SB, Lot #LC05DE2304), and rat C-KIT (SB, Lot #LC06SE1787) 20 μg was fixed on a PEG (Reichert, USA) chip. Thereafter, after flowing 2G4 antibody by concentration, the $K_D$ value, which is the affinity for C-KIT, was analyzed using the Scrubber2 program. The $K_D$ value is obtained by dividing kd by ka, and the lower the value means the greater the binding ability to the target.

The results are shown in FIG. 9. The 2G4 antibody showed a strong affinity for human C-KIT with a $K_D$ value of about $2.8237(\pm 0.9) \times 10^{-12}$ M. The affinity for humans was highest, followed by mice and rats.

Example 6. Domain Mapping

The deletion variants (Q26-P520. D113-P520 Δdomain I, A207-P520 Δdomain I-II, K310-P520 Δdomain I-III) of the human C-KIT gene (NM_000222) were tagged with FLAG at the c-terminus and then were transfected with HEK293. Then, after secretion into the culture medium, these were purified using the FLAG antibody beads (Sigma-Aldrich). Then, ELISA was performed.

Figure 10:
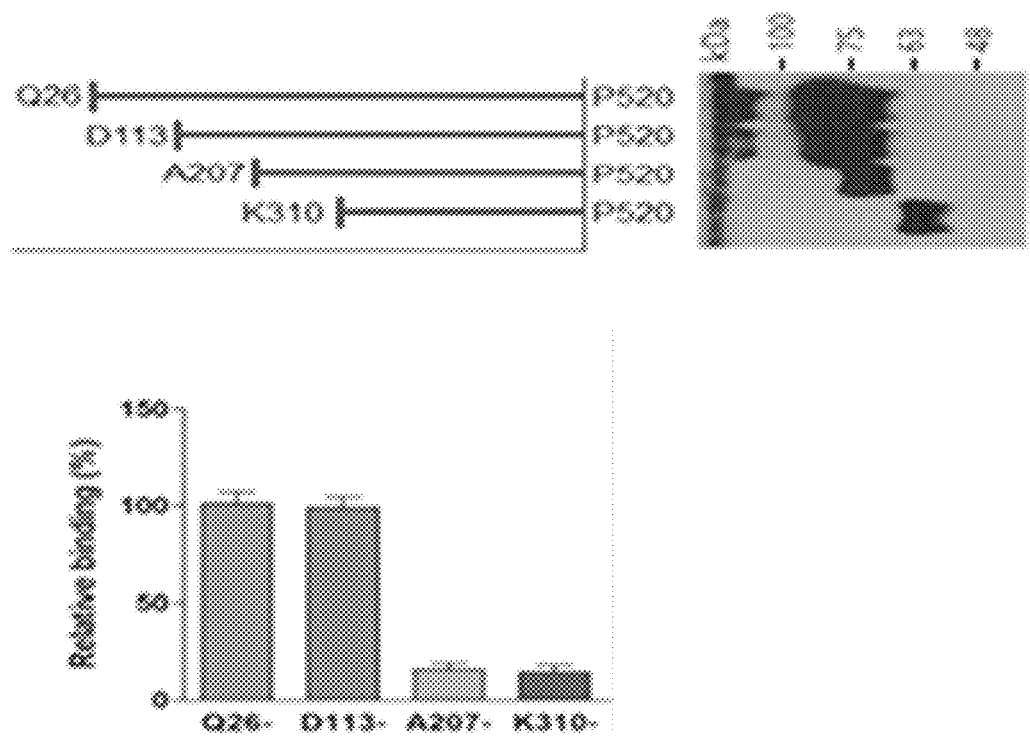
FIG. 10 shows the experimental results for confirming the C-KIT binding domain of the 2G4 antibody.

As shown in FIG. 10, the 2G4 antibody did not recognize C-KIT when domain II was deleted, and from this, it was proved that the specific binding site for C-KIT of the 2G4 antibody was domain II.

Comparative Example 1. Comparison of In Vivo Efficacy Using a Mouse Model

As an animal model for proliferative diabetic retinopathy and premature retinopathy, a widely used mouse oxygen-induced retinopathy (OIR) model was used. Abnormal blood vessels are formed when C57BL/6 mice are exposed to a 75% high oxygen environment for 5 days from 7 days after birth.

C57BL/6 mice were exposed to a 21% oxygen environment from 0 to 7 days after birth, and to a 75% high oxygen environment from 7 to 12 days after birth. On the 12th day after birth, 2G4 antibody (2 μg/eye) and Eylea (2 μg/eye) were injected intravitreally in the right eye, respectively, and PBS was injected into the left eye and compared as a control group. Then, from the 12th to the 17th after birth, they were exposed to an oxygen environment of 21% again, and sacrificed on the 17th day after birth.

Figure 11:
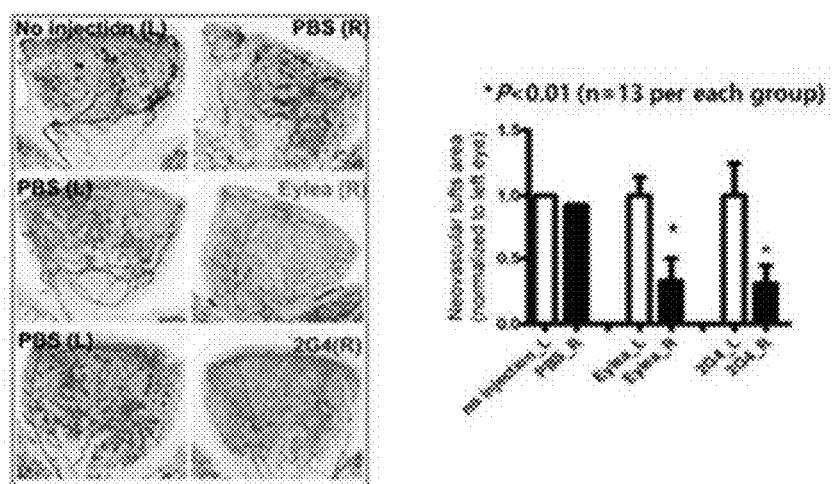
FIG. 11 shows the results of comparing the ability to inhibit abnormal angiogenesis of 2G4 antibody and commercially available Eylea using a mouse oxygen-induced retinopathy model.

As a result, as shown in FIG. 11, abnormal angiogenesis inhibition was observed in the right eye injected with the 2G4 antibody and Eylea (2 μg/eye), and the degree was confirmed to be at the equivalent level.

Comparative Example 2. Comparison of In Vivo Efficacy Using a Rat Model

A macular degeneration model was constructed using brown Norway rats.

CNV (choroidal neovasculanzation) in the rat's eye was induced by using a laser. At the same time, 2G4 antibody (6.28 μg/eye) and Eylea (10 μg/eye) were injected intravitreally at a dose of 4 μl/eye, respectively. A group injected with an IgG antibody (10 μg/eye) at a dose of 4 μl/eye was used as a control.

Figure 12:
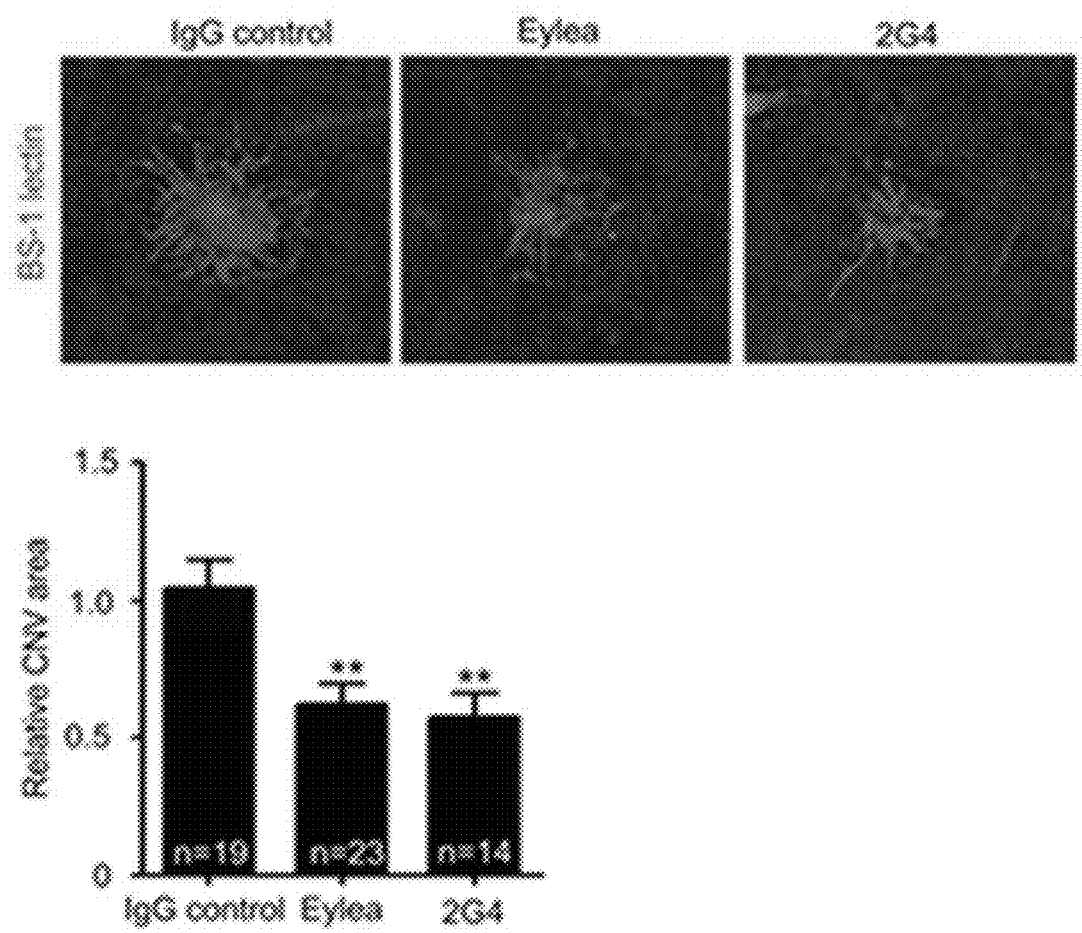
FIG. 12 shows the results of comparing the ability to inhibit abnormal angiogenesis of 2G4 antibody and commercially available Eylea using a Brown Norwegian rat macular degeneration model.

FIG. 12 shows the results of analysis using the BS-1 lectin after 14 days. Abnormal angiogenesis caused by macular degeneration was significantly inhibited in both the Eylea group and the 2G4 antibody group. In particular, the 2G4 antibody showed an equivalent level of efficacy even though the dose concentration was lower than that of Eylea, and it indicates that the 2G4 antibody is more effective than Eylea.

Example 7. SCF/C-KIT Signaling Inhibitory Ability by 2G4 Antibody

Figure 13:
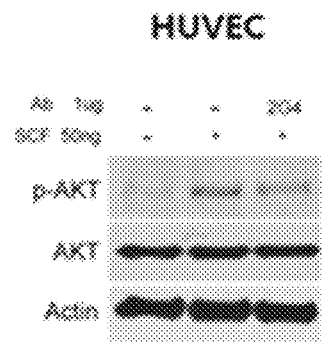
FIG. 13 shows the inhibitory ability of 2G4 antibodies to AKT phosphorylation by SCF in HUVEC cell lines.

SCF/C-KIT signaling is known to basically induce phosphorylation of AKT. As seen in FIG. 13, it was confirmed that AKT phosphorylation was increased when SCF was treated with HUVEC. On the other hand, it was confirmed that AKT phosphorylation was decreased by the 2G4 antibody.

Figure 14:
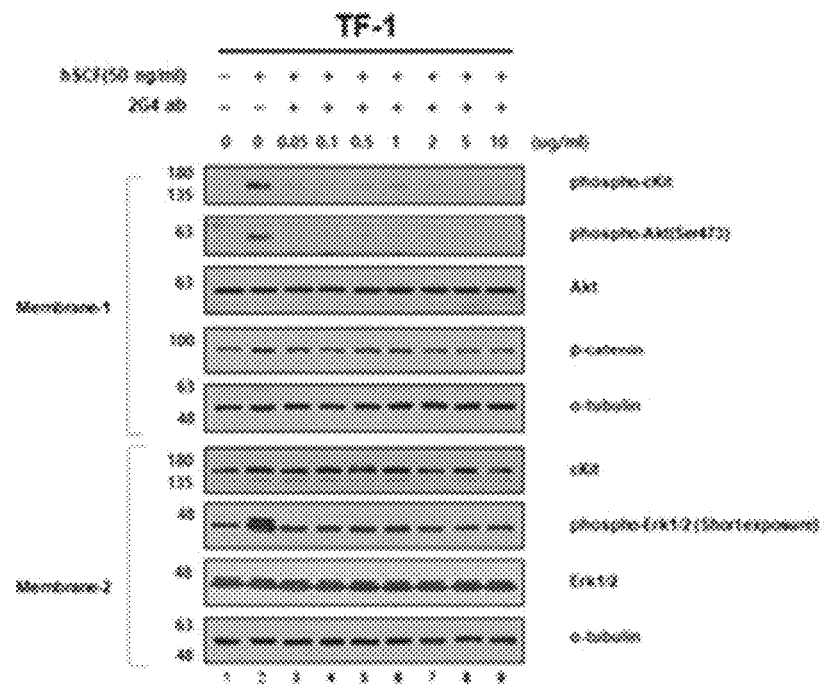
FIG. 14 shows the inhibitory ability of 2G4 antibodies to AKT phosphorylation, C-KIT phosphorylation, ERK 1/2 phosphorylation, and β-catenin in TF-1 cell line, thereby showing the inhibition of leukemia cell proliferation.

In addition, it can be seen from FIG. 14 that AKT phosphorylation by SCF is inhibited by the 2G4 antibody in the leukemia cell line TF-1. Moreover, it can be seen from FIG. 14 that phosphorylation of ERK1/2 and phosphorylation of C-KIT by SCF are also inhibited. β-catenin is an AKT downstream signal, and is known to be an important factor in cell proliferation. It can be seen in FIG. 14 that the 2G4 antibody inhibits the increase of β-catenin by SCF in a concentration-dependent manner, which means that the 2G4 antibody significantly inhibits the proliferation of the leukemia cell line TF-1. Leukemia has many C-KIT mutations, and thus the resistance or tolerance on anticancer drug is often found. However, the antibody according to the present invention can show a preventive or therapeutic effect against leukemia, and thus it can overcome the limitations of prior anticancer drugs.

Example 8. Proliferation Inhibitory Ability of HUVEC and TF-1 Cell by 2G4 Antibody 2G4 antibodies were pretreated on TF-1 and HUVEC for 30 minutes at different concentrations (0, 0.1, 1, 5, 10 μg/ml). Thereafter, 50 ng/ml of SCF was treated, and after 36 hours, the number of cells was measured to compare the cell proliferation rate.

Figure 15:
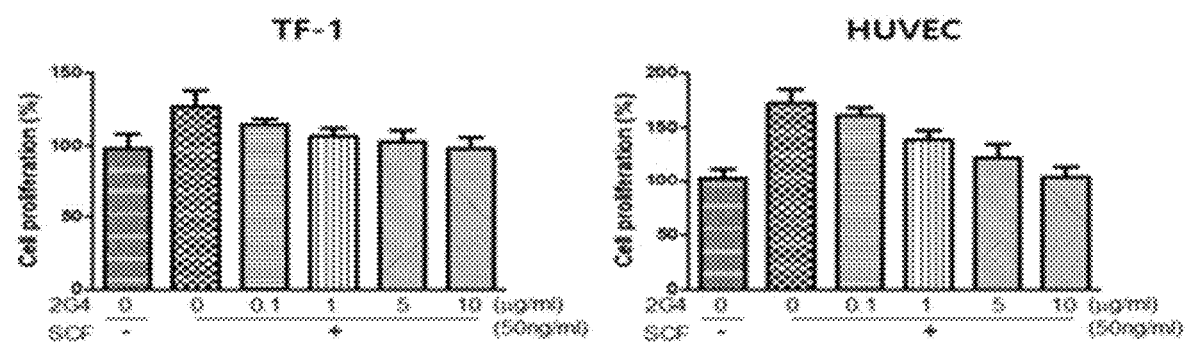
FIG. 15 shows the cell proliferation inhibitory ability of HUVEC and TF-1 by the 2G4 antibody.

As shown in FIG. 15, the SCF-treated group increased the number of TF-1 cells by about 26% and the number of HUVEC cells by about 70% compared to the negative control group. On the other hand, in the group treated with 2G4 antibody, cell proliferation by SCF was inhibited in a concentration-dependent manner in both TF-1 and HUVEC. This means that the 2G4 antibody has a very good ability to inhibit the proliferation of HUVEC and TF-1 cells.

What is claimed is:

1. An anti-C-KIT antibody or antibody fragment thereof, specifically binding to domain II of C-KIT, wherein the anti-C-KIT antibody or antibody fragment thereof comprises a light chain variable region comprising a light chain CDR1 of SEQ ID NO: 1, a light chain CDR2 of SEQ ID NO: 2, and a light chain CDR3 of SEQ ID NO: 3; and a heavy chain variable region comprising a heavy chain CDR1 of SEQ ID NO: 4, a heavy chain CDR2 of SEQ ID NO: 5, and a heavy chain CDR3 of SEQ ID NO: 6.

2. The anti-C-KIT antibody or antibody fragment thereof according to claim 1, wherein the anti-C-KIT antibody or antibody fragment thereof comprises a light chain variable region comprising the amino acid sequence of SEQ ID NO: 7; and a heavy chain variable region comprising the amino acid sequence of SEQ ID NO: 8.

3. The anti-C-KIT antibody or antibody fragment thereof according to claim 1, wherein the anti-C-KIT antibody or antibody fragment thereof comprises a human IgG1-derived constant region.

4. A nucleic acid encoding the anti-C-KIT antibody or antibody fragment thereof of claim 1.

5. The nucleic acid according to claim 4, the nucleic acid comprises (i) SEQ ID NOs: 9 to 14, (ii) SEQ ID NOs: 15 and 16, (iii) SEQ ID NOs: 17 to 22, or (iv) SEQ ID NOs: 23 and 24.

6. A vector comprising the nucleic acid of claim 4.

7. A cell transformed with the vector of claim 6.

8. A method for treating an angiogenesis-related disease, comprising administering the anti-C-KIT antibody or antibody fragment thereof of claim 1 to a patient in need thereof, wherein the angiogenesis-related disease is selected from the group consisting of cancer, leukemia, ophthalmic vascular diseases, rheumatoid arthritis, psoriasis, chronic wounds, chronic inflammation, hemangioma, hemangiofibroma, vascular malformations, arteriosclerosis, vascular adhesions, vasculitis, pyogenic granuloma, blister diseases, pulmonary hypertension, asthma, nasal polyps, infectious diseases, inflammatory bowel disease, periodontal disease, peritoneal adhesions, endometriosis, uterine bleeding, ovarian cysts, osteomyelitis, osteitis, sepsis and autoimmune diseases.

9. The method according to claim 8, the cancer is selected from a group consisting of bone cancer, lung cancer, brain cancer, neck cancer, thyroid cancer, parathyroid cancer, non-small cell lung cancer, gastric cancer, liver cancer, pancreatic cancer, skin cancer, intradermal or intraocular melanoma, rectal cancer, anal cancer, colon cancer, uterine cancer, ovarian cancer, fallopian tube carcinoma, endometrial carcinoma, cervical carcinoma, vaginal carcinoma, vulvar carcinoma, Hodgkin's disease, esophageal cancer, small intestine cancer, endocrine adenocarcinoma, adrenal cancer, soft tissue sarcoma, urethral cancer, penile cancer, prostate cancer, bladder cancer, kidney cancer, or ureteral cancer, renal cell carcinoma, renal pelvic carcinoma, central nervous system tumor, central nervous system lymphoma, spinal cord tumor, glioblastoma, brain stem glioma, and pituitary adenoma.

10. The method according to claim 8, the ophthalmic vascular diseases is selected from a group consisting of diabetic retinopathy, macular degeneration, senile macular degeneration, glaucoma, glaucoma-related retinal pigment degeneration, choroidal neovascularization, retinopathy of prematurity, corneal dystrophy and retinoschisis.

11. An angiogenesis-related disease diagnostic kit comprising the anti-C-KIT antibody or antibody fragment thereof of claim 1.

* * * * *